(12) United States Patent
Vogel et al.

(10) Patent No.: US 11,208,648 B2
(45) Date of Patent: Dec. 28, 2021

(54) DETERMINING POSITION AND TRANSCRIPTOMES OF BIOLOGICAL CELLS

(71) Applicant: International Business Machines Corporation, Armonk, NY (US)

(72) Inventors: Robert Vogel, San Diego, CA (US); Navneet Dogra, New York, NY (US); Lena Voith von Voithenberg, Adliswil (CH); Aditya Kashyap, Zürich (CH); Govind V. Kaigala, Rüschlikon (CH); Gustavo Alejandro Stolovitzky, Riverdale, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 475 days.

(21) Appl. No.: 16/193,483

(22) Filed: Nov. 16, 2018

(65) Prior Publication Data
US 2020/0157528 A1   May 21, 2020

(51) Int. Cl.
C12N 15/10    (2006.01)
C12Q 1/24     (2006.01)
C12Q 1/6806   (2018.01)

(52) U.S. Cl.
CPC .......... *C12N 15/1037* (2013.01); *C12Q 1/24* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 9,371,598 B2 | 6/2016 | Chee | |
| 9,593,365 B2 | 3/2017 | Frisen et al. | |
| 9,834,814 B2 | 12/2017 | Peter et al. | |
| 2012/0142088 A1* | 6/2012 | Hsiao | A61K 47/6901 435/325 |

FOREIGN PATENT DOCUMENTS

WO   2016162309 A1   10/2016

OTHER PUBLICATIONS

Schwanhäusser, Björn, et al. "Global quantification of mammalian gene expression control." Nature. May 19, 2011;473(7347):337-42. doi: 10.1038/nature10098. 21 pages.
Oyler-Yaniv Alon, et al. "A Tunable Diffusion-Consumption Mechanism of Cytokine Propagation Enables Plasticity in Cell-to-Cell Communication in the Immune System" vol. 46, Issue 4, Apr. 18, 2017, pp. 609-620. 13 pages.
Gregor, Thomas, et al. "Probing the Limits to Positional Information." Cell 130, 153-164, Jul. 13, 2007. 12 pages.
Hanahan, Douglas, et al. "Hallmarks of Cancer: The Next Generation." Cell, vol. 144, Issue 5, Mar. 4, 2011, pp. 646-674. 29 pages.
Bergers, Gabriel, et al. "Benefits of targeting both pericytes and endothelial cells in the tumor vasculature with kinase inhibitors." J. Clin. Invest. 111:1287-1295 (2003). doi:10.1172/JCI200317929. 9 pages.
Noy, Roy, et al. "Tumor-Associated Macrophages: From Mechanisms to Therapy." Immunity Review, 41, Jul. 17, 2014. 13 pages.
Sharma, Padmanee, et al. "Immune checkpoint targeting in cancer therapy: toward combination strategies with curative potential." Cell, vol. 161, Issue 2, Apr. 9, 2015, pp. 205-214. 10 pages.
Kashyap, Aditya, et al. "Selective local lysis and sampling of live cells for nucleic acid analysisusing a microfluidic probe." Scientific Reports, Jul. 14, 2016. 10 pages.
Casasent, Anna K., et al. "Multiclonal Invasion in Breast Tumors Identified by Topographic Single Cell Sequencing." Cell, vol. 172, Issues 1-2, Jan. 11, 2018, pp. 205-217.e12. 26 pages.
Qasaimeh, Mohammad A., et al. "Microfluidic Probes to Process Surfaces, Cells, and Tissues." Selected Topics in Nanomedicine, pp. 257-279 (2013). 23 pages.
Satija, Rahul, et al. "Spatial reconstruction of single-cell gene expression data." Nature Biotechnology, Apr. 13, 2015. 14 pages.
Sachs, Karen, et al. "Causal Protein-Signaling Networks Derived from Multi parameter Single-Cell Data." Science, vol. 308, Apr. 22, 2005. 9 pages.
Bendall, Sean C., et al. "Single-Cell Mass Cytometry of Differential Immune and Drug Responses Across a Human Hematopoietic Continuum." Science 332, 687 (2011). 11 pages.
Stoeckius, Marlon, et al. "Simultaneous epitope and transcriptome measurement in single cells." Nat Methods. Sep. 2017;14(9):865-868. doi: 10.1038/nmeth.4380. Epub Jul. 31, 2017. 10 pages.
Peterson, Vanessa M., et al. "Multiplexed quantification of proteins and transcripts in single cells." Nature Biotechnology, Aug. 30, 2018. 10 pages.
Chattopadhyay, Pratip K., et al."Quantum dot semiconductor nanocrystals for immunophenotyping by polychromatic flow cytometry." Nature Medicine, vol. 12, No. 8, Aug. 2006. 6 pages.
Macosko, Evan Z., et al. "Highly Parallel Genome-wide Expression Profiling of Individual Cells Using Nanoliter Droplets." Cell 161, 1202-1214 May 21, 2015. 14 pages.
Gierahn, Todd M., et al. "Seq-Well: portable, low-cost RNA sequencing of single cells at high throughput." Nature Methods, Feb. 13, 2017. 8 pages.
Kashyap, Aditya, et al. "Rapid Subtractive Patterning of Live Cell Layers with a Microfluidic Probe." Vis. Exp. (115), e54447, doi: 10.3791/54447 (2016) 10 pages.

(Continued)

*Primary Examiner* — Christopher M Gross
(74) *Attorney, Agent, or Firm* — Amin, Turocy & Watson, LLP

(57) ABSTRACT

Techniques regarding measuring a position and transcriptome of one or more cells from a biological sample are provided. For example, one or more embodiments described herein can comprise a method, which can comprise covalently bonding a probe to a molecular structure located on a cell to label the cell according to a position of the cell with regards to a biological sample comprising the cell. The probe comprises an oligonucleotide sequence that can be indicative of the position.

18 Claims, 11 Drawing Sheets

(56) References Cited

OTHER PUBLICATIONS

Zhu, Y.Y., et al. "Reverse Transcriptase Template Switching: A SMART Approach for Full-Length cDNA Library Construction." BioTechniques 30:892-897 (Apr. 2001). 6 pages.

Tanese, Naoko, et al. "Domain structure of the Moloney murine leukemia virus reverse transcriptase: mutational analysis and separate expression of the DNA polymerase and RNase H activities." Proceedings of the National Academy of Sciences of the United States of America, vol. 85, No. 6 (Mar. 15, 1988), pp. 1777-1781. 6 pages.

Klein, Allon M., et al. "Droplet Barcoding for Single-Cell Transcriptomics Applied to Embryonic Stem Cells." Cell, vol. 161, Issue 5, May 21, 2015, pp. 1187-1201. 16 pages.

Bose, Sayantan, et al. "Scalable microfluidics for single-cell RNA printing and sequencing." Bose et al. Genome Biology (2015) 16:120. 16 pages.

Lovchik, Robert D., et al. "Micro-immunohistochemistry using a microfluidic probe†." Lab Chip, 2012, 12, 1040. 5 pages.

Huber, D., et al. "Micro fluorescence in situ hybridization (µFISH) for spatially multiplexed analysis of a cell monolayer." Biomed Microdevices (2016) 18: 40. 8 pages.

* cited by examiner

DETERMINING POSITION AND TRANSCRIPTOMES OF BIOLOGICAL CELLS

BACKGROUND

The subject disclosure relates to one or more methods for determining the position and transcriptomes of biological cells, and more specifically, to labeling one or more cells with a molecular probe that can delineate a position within a biological sample, and determining one or more transcriptomes of the labelled cells.

The successful functioning of multicellular biological organisms relies upon the coordinated functions of tens of thousands molecular constituents of individual cells and the interactions among functionally distinct cells. Importantly, the molecular composition of cells is dynamic (e.g., constantly changing in response to cell-to-cell interactions and environmental conditions). Cell-to-cell interactions are often local, manifesting from either physical cell-to-cell contact or by short length-scale paracrine signaling. Thus, the state of a biological system is defined by the relative positions of each cell and each cell's high dimensional molecular composition.

There are many biological examples in which position and cell-to-cell interactions drive healthy and disease states. For example, the patterning in *Drosophila melanogaster* requires spatially coordinated expression of many genes across the anterior posterior axis of the multi-nucleated zygote. In diseases such as cancer, specific tumor cell subpopulations can recruit adjacent normal endothelial, fibroblast, and immune infiltrating cells to support tumor progression. The relevance of cell positioning has motivated the development of therapeutic agents that target the tumor co-opted normal cells, including: platelet-derived growth factor ("PDGFR") inhibitors to target PDGFR+ pericytes; and small molecule inhibitors or neutralizing antibodies of colony-stimulating factor 1 ("CSF1") receptor to target macrophages.

Concomitant spatial and molecular measurements are of interest to basic biological and translational biomedical sciences. To date, concomitant measurements of molecular and positional information are most commonly collected by microscopy. Here samples are prepared by either cell culture, or by mounting thin slices of paraffin embedded tissue onto microscope slides. Specific molecular and positional information are then measured by taking images of samples treated with either enzymatically or fluorescently labeled antibodies that specifically bind to the molecular target of interest. In the case of digital images, the sensors pixel positions capture the spatial relationship of each cell, while the signal intensity of each pixel is reflective of the local density of the antibody's target molecule.

Other conventional methods attempt to achieve concomitant spatial and molecular measurements by separating the task into two steps: concomitant harvesting of single cells and recording position; and using these single cell samples for molecular profiling. However, with such a strategy, each cell needs to be stored in physically distinct aliquots and consequently suffers with issues in scalability. Indeed, it is challenging to implement such a technique when millions of distinct cells need to be stored and processed separately for molecular profiling.

Additional conventional methods loosely associate endogenous nucleotide sequences to individual cells. This association is done by incorporating single cell boundaries from bright field, or similar, images with the position of the captured oligonucleotide barcodes. In addition to the complexities in developing software to robustly define cell boundaries, this approach suffers from diffusion of the endogenous nucleotide sequences once cells are lysed. In consequence, nucleotide sequences from one cell can diffuse and hybridize with a capture nucleotide sequence that is associated to its neighbor instead.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein methods that can determine the position and transcriptomes of individual biological cells are described.

According to an embodiment, a method is provided. The method can comprise covalently bonding a probe to a molecular structure located on a cell to label the cell according to a position of the cell with regards to a biological sample comprising the cell. The probe comprises an oligonucleotide sequence that can be indicative of the position. An advantage of such a method can be that the cell can be labeled with a molecular marker rather than by an image-based analysis.

In some examples, the method can further comprise dissociating the cell from the biological sample. Also, the method can comprise preparing a complementary deoxyribonucleic acid library regarding the cell and the oligonucleotide sequence that can be indicative of the position of the cell. An advantage of such a method can be that the cell can be labeled with its spatial positioning within the biological sample prior to dissociation.

According to another embodiment, a method is provided. The method can comprise distributing, by a liquid cargo delivery device, a molecular probe to a cell comprised within a biological sample. The method can also comprise covalently bonding the molecular probe to a surface structure of the cell. The molecular probe can comprise an oligonucleotide sequence that is associated with a position within the biological sample. An advantage of such a method can be that position information of a cell can be recorded while maintaining an association of endogenous nucleotide sequences to individual cells.

In some examples, the molecular probe can further comprise a functional group that can chemically react with the surface structure of the cell. The molecular probe can also comprise a polymerase chain reaction handle that can enable a polymerase chain reaction amplification. Moreover, the molecular probe can comprise a bonding oligonucleotide sequence that can complement another oligonucleotide sequence of a distinctly coded microparticle. An advantage of such a method can be that both position information and ribonucleic acid sequences can be captured by a single distinctly coded microparticle to facilitate sample preparation using one or more a Moloney murine leukemia virus reverse transcriptase ("MMLV RT") technologies.

According to another embodiment, a method is provided. The method can comprise recording a position of a cell within a biological sample and a transcriptome of the cell. The cell can be labeled based on the position by covalently bonding a molecular probe to a surface structure of the cell. An advantage of such a method can be that, by combining high resolution spatial and single cell transcriptomic information, the method can provide a complex analysis of the cell's biological functions.

In some examples, the method can also comprise distributing, by a liquid cargo delivery device, the molecular probe to the position. Further, the molecular probe comprises an oligonucleotide sequence that can be associated with the position. An advantage of such a method can be that a composition of the molecular probe can be customized according to the position on the biological sample at which the molecular probe is distributed.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the above problems with conventional concomitant spatial and molecular measurements; the present disclosure can be implemented to produce a solution to one or more of these problems in the form of one or more methods that can label a cell based on the cell's position within a biological sample while also associating endogenous nucleotide sequences to the cell. Advantageously, position information can be retained by the various embodiments described herein without compromising the number of measurement channels used for molecular profiling. Further, one or more embodiments can advantageously add position labeling to one or more cells without precluding the detection of ribonucleic acid ("RNA") sequences. Additionally, the position-specific labeling techniques described herein can allow the pooling of multiple cells together for subsequent processing and preparation for sequencing.

Various embodiments described herein can comprise methods regarding simultaneously recording position and the transcriptomic information of individual cells. For example, one or more embodiments described herein can comprise the use of one or more devices for delivering solutions to small spatial scales (e.g., microfluidic probes) to deliver custom oligonucleotide sequences functionalized to indiscriminately bond to proteins located on cell surfaces. For each position on a biological sample that the delivery device visits, a unique oligonucleotide sequence can be delivered. These oligonucleotide sequences can in effect be a label of the cellular position in culture or in a tissue section. Once the one or more delivery devices complete distribution of respective oligonucleotide sequences to one or more positions on the biological sample, one or more cells comprised with the biological sample can be harvested and sent for single cell sequencing, which can be performed using one or more MMLV RT technologies. Additionally, the transcriptomic information collected by the single cell sequencing and/or the position information conveyed by the oligonucleotide sequence bonded to the cell can be recorded in silico.

Figure 1:
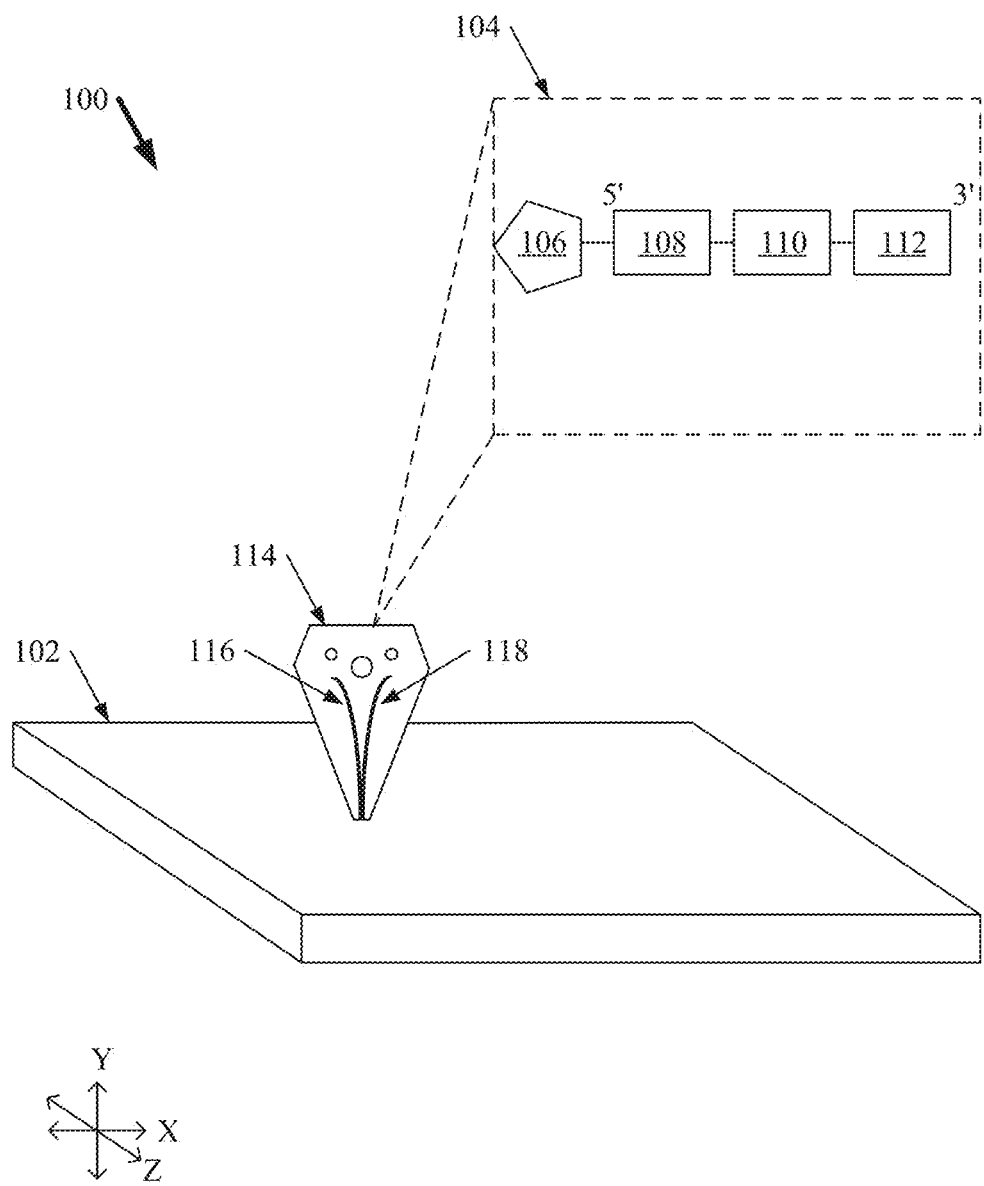
FIG. 1 illustrates a diagram of an example, non-limiting cell labeling process that can facilitate recording a concomitant of positional and transcriptomic information regarding one or more cells within a biological sample in accordance with one or more embodiments described herein.

FIG. 1 illustrates a diagram of an example, non-limiting labeling process 100 in accordance with one or more embodiments described herein. During the labeling process 100, one or more cells comprised within a biological sample 102 can be labeled with one or more molecular probes 104 based on the cells' position, wherein a composition of the one or more molecular probes 104 can be associated with a position within the biological sample 102. For example, the labeling process 100 can comprise labeling one or more cells comprised within the biological sample 102 with position information by delivering one or more molecular probes 104 to the one or more cells, wherein the one or more molecular probes 104 can covalently bond to the one or more cells and encode a position at which the one or more cells are located within the biological sample 102. The biological sample 102 can comprise, for example: a cell culture (e.g., comprising eukaryotic and/or prokaryotic cells), a tissue sample (e.g., a biopsy, formalin-fixed paraffin-embedded ("FFPE"), and/or frozen tissue), a combination thereof, and/or like.

The one or more molecular probes 104 can comprise a functionalized oligonucleotide sequence having four sections. A first section 106 of the one or more molecular probes 104 can comprise one or more functional groups having a chemical affinity to bond to one or more molecular structures ubiquitously found on one or more surfaces of one or more cells. A second section 108 of the one or more molecular probes 104 can comprise a universal polymerase chain reaction ("PCR") handle that can enable a PCR amplification. A third section 110 of the one or more molecular probes 104 can comprise a position-specific oligonucleotide sequence. Also, a fourth section 112 of the one or more molecular probes 104 can comprise a bonding oligonucleotide sequence that can facilitate hybridization.

The one or more functional groups comprised within the first section 106 can include one or more compounds that can covalently bond with one or more molecular structures located on a surface of one or more cells comprised with the biological sample 102. In one or more embodiments, the one or more functional groups can comprise one or more compounds that are: amine reactive, thiol reactive, carboxylic acid reactive, aldehyde reactive, photoreactive crosslinking, a combination thereof, and/or the like. For example, the one or more functional groups can comprise: an N-hydroxysuccinimide ester, a sulfo-N-hydroxysuccinimide ester, an imidoester, a fluorophenyl ester, an epoxide, an isothiocyanate, an isocyanate, a sulfonyl chloride, an aldehyde, a carbodiimide, an acyl azide, an anhydride, a fluorobenzene, a carbonate, a combination thereof, and/or the like. For instance, the one or more functional groups can couple with one or more side chains of an amino acid, such as the primary amines of arginine and/or lysine. In another example, the one or more functional groups can comprise maleimide, a haloacetyl, a pyridyl disulfide, a combination thereof, and/or the like. For instance, the one or more functional groups can couple with a thiol group, such as the thiol group of cysteine. In another example, the one or more functional groups can comprise a carbodiimide that can covalently bond with aspartic acid and/or glutamic acid through carboxylic acid coupling. In a further example, the one or more functional groups can covalently bond to one or more carbonyl groups of glycoproteins through hydrazine or alkoxyamine coupling. In various embodiments, the one or more functional groups can covalently bond to a protein or a lipid located on a surface of one or more cells comprised within the biological sample 102. Further, in one or more embodiments, the one or more functional groups can bond indiscriminately to any surface protein and/or lipid comprising a structure compatible with the chemical affinity of the subject functional group. For example, a single functional group can have a chemical affinity to bond to multiple types of proteins and/or lipids. For instance, the one or more functional groups can bond non-specifically to any surface protein and/or lipid that can facilitate the chemical reactivity of the one or more functional groups, without a particular preference to a certain protein and/or lipid.

The PCR handle comprised with the second section 108 can comprise a priming site for downstream PCR amplification of the molecular probe 104. The position-specific oligonucleotide sequence comprised within the third section 110 can be a nucleotide sequence that is associated with a particular position within the biological sample 102. A length of the position-specific oligonucleotide sequence can depend on the number of positions encoded by the labeling process 100. For example, the length of the position-specific oligonucleotide sequence can be characterized by Equation 1 below.

$$L \geq \log 4(N) \qquad (1)$$

Wherein "L" can represent the length of the position-specific oligonucleotide sequence (e.g., the number of nucleotides comprising the position-specific oligonucleotide sequence), and "N" can comprise the number positions that can be encoded by the labeling process 100.

The bonding oligonucleotide sequence comprised within the fourth section 112 can be a nucleotide sequence that is complementary to another oligonucleotide sequence comprised within an RNA capturing microparticle. Due at least to the complementary nature of the bonding oligonucleotide sequence, the bonding oligonucleotide sequence can couple the molecular probe 104 to the RNA capturing microparticle. As used herein the term "RNA capturing microparticle" can refer to a microparticle comprising one or more oligonucleotide primers that can capture RNA and/or single strand deoxyribonucleic acid ("DNA") to facilitate a synthesis of complementary DNA ("cDNA") by one or more MMLV RT technologies or one or more techniques similar to MMLV RT. The specific nucleotide sequence of the bonding oligonucleotide sequence can depend on the RNA capturing microparticle that can be used to collect transcriptomic information of one or more cells labeled by the labeling process 100. For example, wherein the subject RNA capturing microparticle comprises a repeating thymine sequence, the bonding oligonucleotide sequence can comprise a repeating adenine sequence.

As shown in FIG. 1, the one or more molecular probes 104 can be delivered to the biological sample 102 by one or more delivery devices 114. The one or more delivery devices 114 can deliver, with high spatial resolution, fluid cargo (e.g., comprising the one or more molecular probes 104) to one or more cells comprised within the biological sample 102. For example, the one or more delivery devices 114 can be microfluidic probes (e.g., as shown in FIG. 1). As used herein, the term "microfluidic probe" can refer to a non-contact, scanning platform that can hydrodynamically localize as little as 100 picoliters of liquid cargo (e.g., comprising the one or more molecular probes 104) with micrometer precision.

In one or more embodiments, the one or more delivery devices 114 can comprise a microfluidic probe comprising a head having two microchannels with apertures at an apex (e.g., as shown in FIG. 1). A first microchannel 116 can be used for injecting a processing liquid (e.g., comprising the one or more molecular probes 104), while a second microchannel 118 can be used for aspirating the injected processing liquid together with an immersion liquid. During delivery of the one or more molecular probes 104, the apex of the microfluidic probe can be disposed at a fixed distance from the biological sample 102. When the aspiration flow rate is sufficiently higher than the injection flow rate, the processing liquid (e.g., comprising the one or more molecular probes 104) can be confined to a specific position on the biological sample 102 by hydrodynamic flow confinement.

Figure 2:
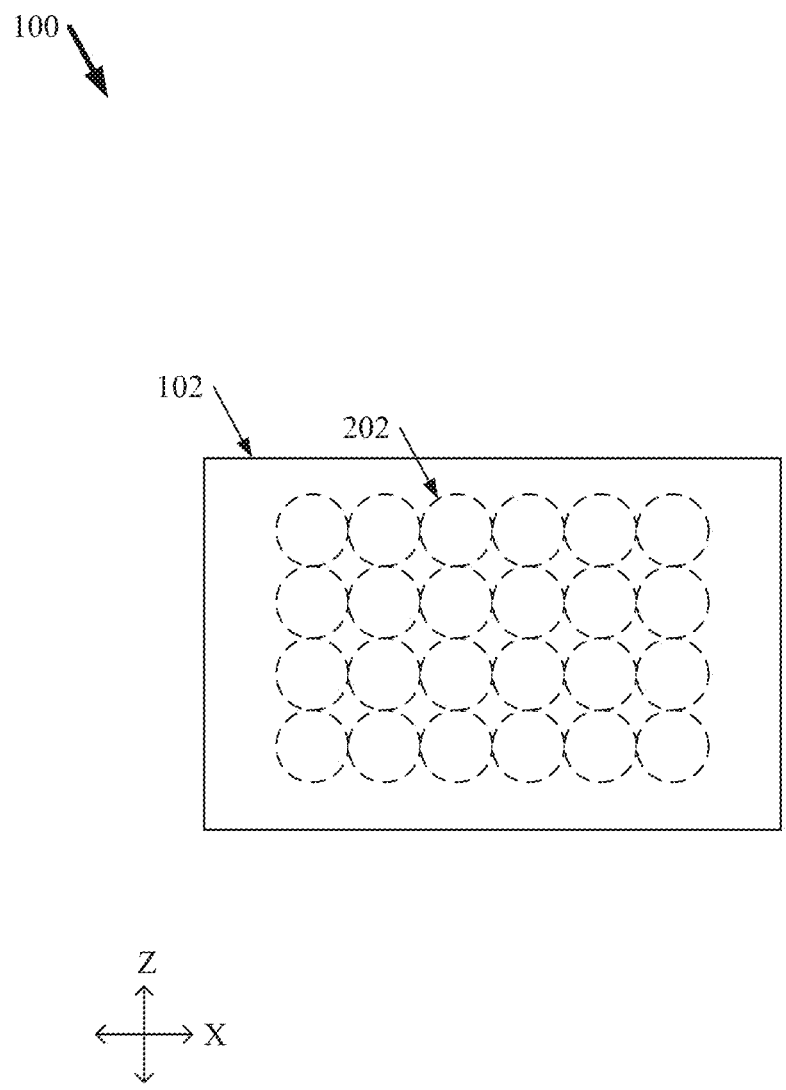
FIG. 2 illustrates a diagram of an example, non-limiting distribution scheme that can delineate the delivery of one or more molecular probes during preparation of a biological sample in accordance with one or more embodiments described herein.

FIG. 2 illustrates a diagram of an example, non-limiting delivery scheme that can be performed by the labeling process 100 in accordance with one or more embodiments described herein. Repetitive description of like elements employed in other embodiments described herein is omitted for sake of brevity. As shown in FIG. 2, the biological sample 102 can comprise one or more regions 202 (e.g., delineated by dashed lines in FIG. 2). The one or more regions 202 can be defined by position information, for example, with regards to the biological sample 102. For instance, the one or more regions 202 can correlate to one or more set of position coordinates (e.g., along the "X" and/or "Z" axes shown in FIG. 2). During the labeling process 100, the one or more delivery devices 114 can deliver one or more molecular probes 104 to the one or more regions 202.

In one or more embodiments, each region 202 can be associated with a unique position-specific oligonucleotide sequence comprised within the third section 110 of the one or more molecular probes 104. One or more molecular probes 104 comprising a position-specific oligonucleotide sequence associated with a respective region 202 can be deposited into the associated region 202 during the labeling process 100 by the one or more delivery devices 114. For example, one or more first molecular probes 104 comprising a first position-specific oligonucleotide sequence can be delivered, by the one or more delivery devices 114, to a first region 202 of the biological sample 102; while one or more second molecular probes 104 comprising a second position-specific oligonucleotide sequence can be delivered, by the one or more delivery devices 114, to a second region 202 of the biological sample 102, wherein the first position-specific oligonucleotide sequence and the second position-specific oligonucleotide sequence can comprise different nucleotide sequences. By delivering multiple molecular probes 104 having a variety of position-specific oligonucleotide sequences, the labeling process 100 can encode cells with the position of a various regions 202 in which the cells are located.

While circular regions 202 are depicted in FIG. 2, the architecture of the distribution scheme implemented by the labeling process 100 is not so limited. For example, the one or more regions 202 can be characterized by various shapes, include polygonal geometries. Additionally, in various embodiments, one or more of the regions 202 can overlap each other to further specify one or more positions in the biological sample 102.

Figure 3:
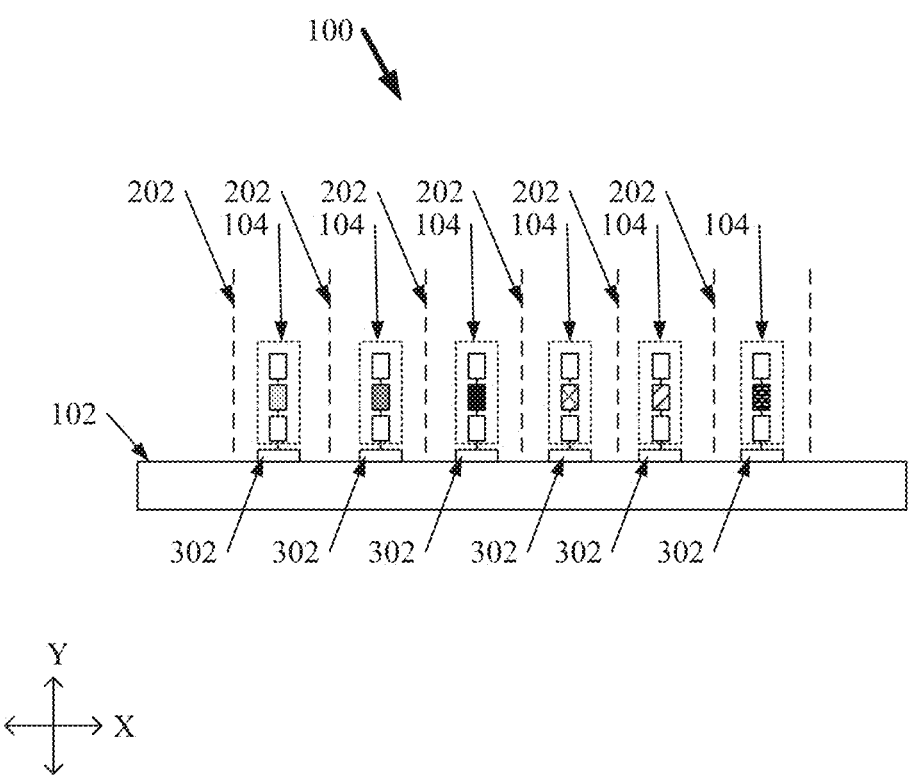
FIG. 3 illustrates a diagram of an example, non-limiting biological sample comprising a plurality of cells labeled according to their position within the biological sample in accordance with one or more embodiments described herein.

FIG. 3 illustrates a diagram of the example, non-limiting biological sample 102 functionalized with a plurality of molecular probes 104 as a result of the labeling process 100 in accordance with one or more embodiments described herein. Repetitive description of like elements employed in other embodiments described herein is omitted for sake of brevity. As shown in FIG. 3, respective position-specific oligonucleotide sequences are depicted with different shading and/or cross-hatching.

FIG. 3 depicts how a unique position-specific oligonucleotide sequence can be delivered to each region 202 of the biological sample 102. When a molecular probe 104 is delivered to a region 202, the one or more functional groups comprised within the first section 106 can facilitate a covalent bond between the molecular probe 104 and a region 202 on the biological sample 102. For example, the one or more functional groups can chemically react with one or more molecular structures (e.g., proteins and/or lipids) of an adherent cell 302 to establish the covalent bond. Thus, the second section 108, the third section 110, and/or the fourth section 112 of the molecular probe 104 can be covalently bonded to the one or more adherent cells 302 (e.g., as shown in FIG. 3).

As shown in FIG. 3, the adherent cells 302 positioned within a region 202 can be covalently bonded to a respective position-specific oligonucleotide sequence associated with that region 202. Thus, delivery of one or more molecular probes 104 to a region 202 can label the one or more adherent cells 302 positioned in the region 202 with the one or more molecular probes 104, thereby bonding a position-specific oligonucleotide sequence to the adherent cells 302 of the region 202. Further, since the position-specific oligonucleotide sequence can have a particular composition associated with the region 202, bonding the position-specific oligonucleotide sequence to the adherent cell 302 encodes position information onto the adherent cell 302. Therefore, adherent cells 302 located in a first region 202 can be labeled with one or more molecular probes 104 encoded (e.g., via the position-specific oligonucleotide sequence) with position information associated with the first region 202; while adherent cells 302 located in a second region 202 can be labeled with one or more molecular probes 104 encoded (e.g., via the position-specific oligonucleotide sequence) with position information associated with the second region 202.

Once the adherent cells 302 in each region 202 are labeled with the one or more molecular probes 104, the one or more adherent cells 302 can be dissociated from the biological sample 102 and transcriptomic information can be collected using one or more single cell sequencing techniques. For example, for each labeled adherent cell 302, single cell cDNA library preparation can be performed using one or more MMLV RT technologies to facilitate one or more single cell RNA sequencing techniques.

For example, one or more cDNA library preparation methods techniques performed to facilitate determination of a molecular profile of the one or more labeled adherent cells 302 can utilize RNA capturing microparticles. However, conventional RNA capturing microparticles are mono-functionalized, wherein the oligonucleotide primers can bond to a single nucleotide sequence. Use of mono-functionalized RNA capturing microparticles in the one or more cDNA library preparation methods can result in competitive bonding between endogenous messenger RNA ("mRNA") and bonding oligonucleotide sequences comprised within the fourth sections 112 of the one or more molecular probes 104. In other words, endogenous mRNA of a labeled adherent cells 302 can compete with molecular probes 104 previously bonded to a surface of the labeled adherent cell 302 for bonding to the mono-functionalized RNA capturing microparticles.

Figure 4:
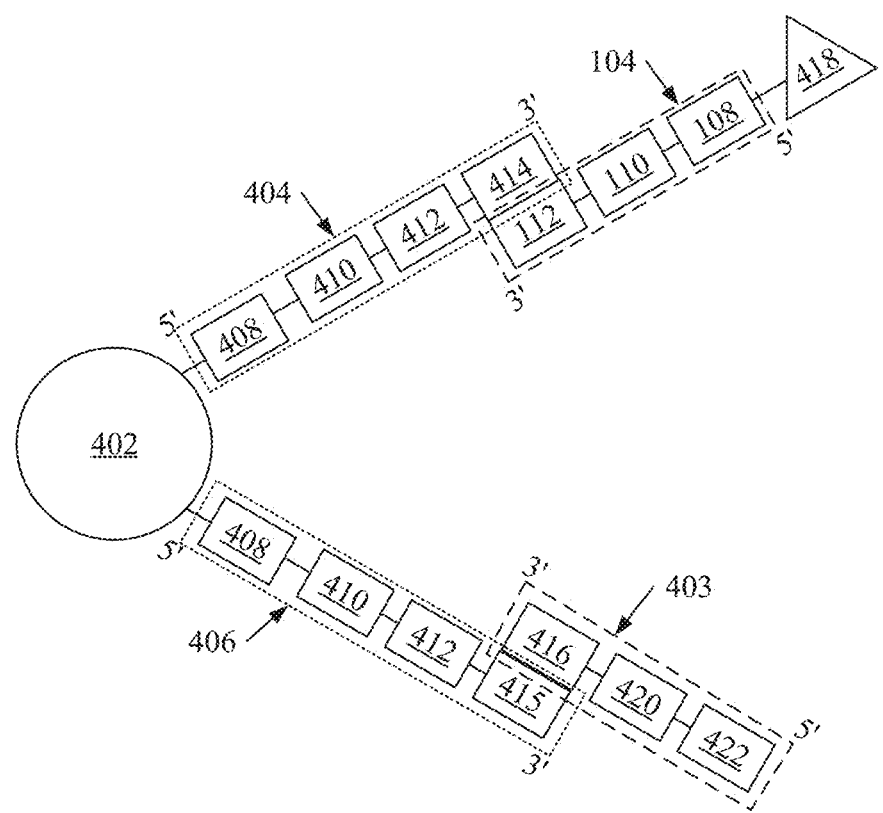
FIG. 4 illustrates a diagram of an example, non-limiting bi-functionalized microparticle that can capture one or more nucleic acid sequences, which can delineate positional and/or transcriptomic information of a given cell in accordance with one or more embodiments described herein.

FIG. 4 illustrates a diagram of an example, non-limiting bi-functionalized RNA capturing microparticle 402 that can facilitate one or more cDNA library preparation methods performed on an adherent cell 302 labeled by the labeling process 100 in accordance with one or more embodiments described herein. Repetitive description of like elements employed in other embodiments described herein is omitted for sake of brevity. Advantageously, the bi-functionalized RNA capturing microparticle 402 can reduce and/or inhibit competitive bonding between endogenous mRNA sequences 403 and the molecular probes 104 during the cDNA library preparation.

As shown in FIG. 4, the bi-functionalized RNA capturing microparticle 402 can comprise a first oligonucleotide primer 404 for capturing a molecular probe 104 and a second oligonucleotide primer 406 for capturing an endogenous RNA sequence 403 (e.g., endogenous mRNA). The oligonucleotide primers of the bi-functionalized RNA capturing microparticle 402 (e.g., the first oligonucleotide primer 404 and the second oligonucleotide primer 406) can comprise a first portion 408, which can include a PCR handle to enable a PCR amplification. Further, in one or more embodiments the PCR handle of the first portion 408 and the second section 108 can have the same composition such that the single cell sequencing technique can PCR amplify cDNA corresponding to cellular positions and endogenous mRNA transcripts in a single step.

Also, the oligonucleotide primers of the bi-functionalized RNA capturing microparticle 402 (e.g., the first oligonucleotide primer 404 and the second oligonucleotide primer 406) can comprise a second portion 410, which can include a cell barcode. The cell barcode can be a cell-specific nucleotide sequence that is constant amongst all the oligonucleotide primers of the bi-functionalized RNA capturing microparticle 402 but different for each bi-functionalized RNA capturing microparticle 402 used in the one or more sequencing techniques. For example, a first bi-functionalized RNA capturing microparticle 402 comprising a first cell barcode can be used to capture molecular probes 104 and/or mRNA sequences of a first labeled adherent cell 302; while a second bi-functionalized RNA capturing microparticle 402 comprising a second cell barcode can be used to capture molecular probes 104 and/or mRNA sequences of a second labeled adherent cell 302, wherein the first bar code and the second bar code can comprise different nucleotide sequences.

Further, the oligonucleotide primers of the bi-functionalized RNA capturing microparticle 402 (e.g., the first oligonucleotide primer 404 and the second oligonucleotide primer 406) can comprise a third portion 412, which can include a unique molecular identifier ("UMI"). Each UMI can comprise a nucleotide sequence unique to the oligonucleotide primer the given UMI is comprised within. In other words, the UMI of each oligonucleotide primer can comprise a different nucleotide sequence. In one or more embodiments, the bi-functionalized RNA capturing microparticle 402 can comprise a plurality of UMIs, wherein at least one UMI can be comprised within each oligonucleotide primer of the bi-functionalized RNA capturing microparticle 402. The UMIs can be used for normalizing gene counts during one or more computation data processing. For example, the UMIs can used to identify PCR duplicates during the one or more single cell sequencing techniques.

Moreover, the first oligonucleotide primer 404 can comprise a first capturing portion 414, which can include a first capturing oligonucleotide sequence. Also, the second oligonucleotide primer 406 can comprise a second capturing portion 415, which can include a second capturing oligonucleotide sequence. In various embodiments, the first capturing oligonucleotide sequence of the first oligonucleotide primer 404 can be different than the second capturing oligonucleotide sequence of the second oligonucleotide primer 406. For example, the first capturing oligonucleotide sequence of the first oligonucleotide primer 404 can be complementary to the bonding oligonucleotide sequence of the one or more molecular probes 104; whereas the second capturing oligonucleotide sequence of the second oligonucleotide primer 406 can be complementary to a tail portion 416 of the one or more endogenous RNA sequences 403.

For instance, the second capturing oligonucleotide sequence of the second oligonucleotide primer 406 can comprise a repeating thymine sequence to complement a repeating adenine sequence of the tail portion 416 of the one or more endogenous RNA sequences 403. Further, the bonding oligonucleotide sequence of the one or more molecular probes 104 can be different than the nucleotide sequence of the tail portion 416 of the one or more endogenous RNA sequences 403. Thus, wherein the second capturing oligonucleotide sequence of the second oligonucleotide primer 406 comprises a repeating thymine sequence, the first capturing oligonucleotide sequence of the first oligonucleotide primer 404 can comprise a nucleotide sequence that is other than repeating thymine and a complement to the bonding oligonucleotide sequence of the one or more molecular probes 104. Therefore, the fourth section 112 of the one or more molecular probes 104 can bond to the first oligonucleotide primer 404 and the tail portion 416 of the one or more endogenous RNA sequences 403 can bond to the second oligonucleotide primer 406.

Additionally, as shown in FIG. 4, one or more surface structures 418 from the adherent cell 302 can be bonded to a first end of the molecular probe 104 (e.g., the 5' end), and/or the first oligonucleotide primer 404 can be bonded to a second end of the molecular probe 104 (e.g., the 3' end). For example, the one or more surface structures 418 (e.g., a protein or lipid) could have been previously located on the surface of one or more adherent cells 302 prior to the cDNA library preparation, wherein the one or more functional groups comprised within the first section 106 chemically reacted with the one or more surface structure 418 to facilitate labeling process 100, as described herein.

Also shown in FIG. 4, the one or more endogenous RNA sequences 403 can comprise the tail portion 416 (e.g., bonded to the second oligonucleotide primer 406), a coding region 420, and/or a cap portion 422. The coding region 420 can comprise one or more gene specific nucleotide sequences. The cap portion 422 can comprise, for example, a five-prime ("5'") cap at the 5' end of the one or more endogenous RNA sequences 403 (e.g., as shown in FIG. 4).

In various embodiments, once the RNA capturing microparticles (e.g., bi-functionalized RNA capturing microparticles 402) capture the endogenous RNA sequences 403 and/or molecular probes 104 of a labelled adherent cell 302, cDNA library preparation can be performed using MMLV RT technology. For example, one of ordinary skill in the art will recognize that with regards to the second oligonucleotide primer 406, the MMLV RT technology can synthesize a DNA complement to the nucleotide sequences comprised within the coding region 420 of a captured endogenous RNA sequence 403. Additionally, the MMLV RT technology can append the synthesized cDNA sequence with a poly-cytosine sequence. Subsequently, a template switch oligonucleotide ("TSO") can hybridize with the poly-cytosine sequence, wherein the MMLV RT technology can use the TSO as a template for downstream replications. Further, the synthesized cDNA can be separated from the hybridized endogenous RNA sequences 403 by, for example: ribonuclease H activity of the MMLV RT technology, and/or RNA degradation by sodium hydroxide and heat. The resulting cDNA can then be amplified by one or more PCRs.

Additionally, one of ordinary skill in the art will recognize that with regards to the first oligonucleotide primer 404, the MMLV RT technology can, for example, be used as a DNA polymerase to synthesize a complement to the position-specific oligonucleotide sequence comprised within the molecular probe 104. Further, the synthesized complement to the position-specific oligonucleotide sequence can be separated from the hybridized molecular probe 104 by, for example: ribonuclease H activity of the MMLV RT technology, and/or RNA degradation by sodium hydroxide and heat. The resulting complement to the position-specific oligonucleotide sequence can then be amplified by one or more PCRs. For instance, one or more PCR amplification processes can amplify the cDNA and the complement to the position-specific oligonucleotide sequence simultaneously.

Following the single cell cDNA preparation, one or more single cell sequencing techniques can be performed. Example single cell sequencing methods can include, but are not limited to: drop-seq, seq-well, cyto-seq, a combination thereof, and/or the like. The one or more single cell sequencing can identify: the subject cell by the cell barcode comprised within the RNA capturing microparticles (e.g., bifunctionalized RNA capturing microparticles 402); the initial position of the cell within the biological sample 102 by the complementary position-specific oligonucleotide sequence comprised within the RNA capturing microparticles (e.g., within the first oligonucleotide primer 404 post preparation by the MMLV RT technology), which can originate from the position-specific oligonucleotide sequence of one or more molecular probes 104 bonded to the cell during the labeling process 100; and transcriptome information of the cell by the cDNA comprised within the RNA capturing microparticles (e.g., within the second oligonucleotide primer 406 post preparation by the MMLV RT technology), which can originate from the one or more endogenous RNA sequences 403. Thereby, combination of the labeling process 100 with one or more preparation methods using MMLV RT technology and/or one or more single cell sequencing techniques can collect a concomitant spatial and molecular measurements (e.g., position coordinates and transcriptomes of one or more cells in the biological sample 102), which can be recorded and/or sorted in silico.

Figure 5:
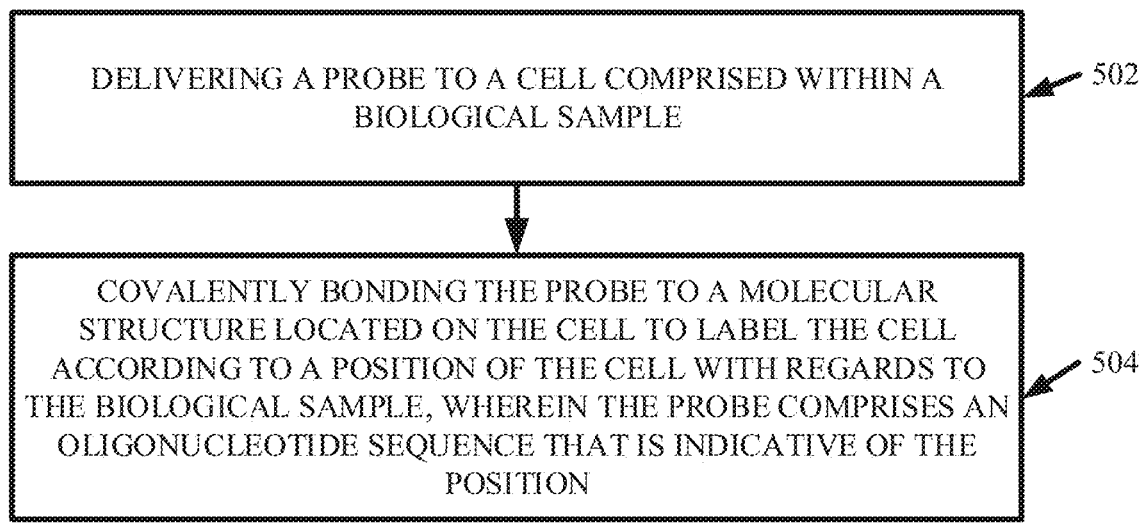
FIG. 5 illustrates a flow diagram of an example, non-limiting method that can facilitate labeling one or more cells based on the cells' position within a biological sample in accordance with one or more embodiments described herein.

FIG. 5 illustrates a flow diagram of an example, non-limiting method 500 that can facilitate labeling one or more cells (e.g., adherent cells 302) with one or more molecular probes 104 that can encode position information describing the cell in accordance with one or more embodiments described herein. Repetitive description of like elements employed in other embodiments described herein is omitted for sake of brevity. For example, in one or more embodiments the method 500 can be performed in accordance with one or more features of the labeling process 100.

At 502, the method 500 can comprise delivering one or more probes (e.g., one or more molecular probes 104) to one or more cells (e.g., one or more adherent cells 302) comprised within a biological sample 102. For example, the delivering at 502 can be performed by one or more delivery devices 114 that can dispense liquid cargo (e.g., comprising the one or more probes). For instance, the one or more delivery devices 114 can be microfluidic probes (e.g., as shown in FIG. 1). In various embodiments, the one or more probes (e.g., one or more molecular probes 104) can be delivered to various regions 202 of the biological sample 102.

At 504, the method 500 can comprise covalently bonding the one or more probes (e.g., one or more molecular probes 104) to one or more molecular structures (e.g., surface structures 418) located on the one or more cells (e.g., one or more adherent cells 302) to label the one or more cells according to a position of the one or more cells with regards to the biological sample 102. The one or more probes (e.g., one or more molecular probes 104) can comprise an oligonucleotide sequence that is indicative of the position of the one or more cells (e.g., a position-specific oligonucleotide sequence, as described herein). For example, wherein the one or more probes are delivered to multiple regions 202 during the delivery at 502, the composition of the oligonucleotide sequence (e.g., the position-specific oligonucleotide sequence) can be dependent on the region 202 in which the probe is delivered.

In various embodiments, the one or more probes can further comprise one or more of the following additional features: a functional group that can have a chemical affinity for the molecular structure, a polymerase chain reaction handle that can enable a polymerase chain reaction amplification, and/or a bonding oligonucleotide sequence that can be a complement to another oligonucleotide sequence of a distinctly coded microparticle (e.g., a complement to the first capturing oligonucleotide sequence of a RNA capturing microparticle). The additional features can facilitate compatibility between the probe and one or more cDNA preparation methods using MMLV RT technology.

Figure 6:
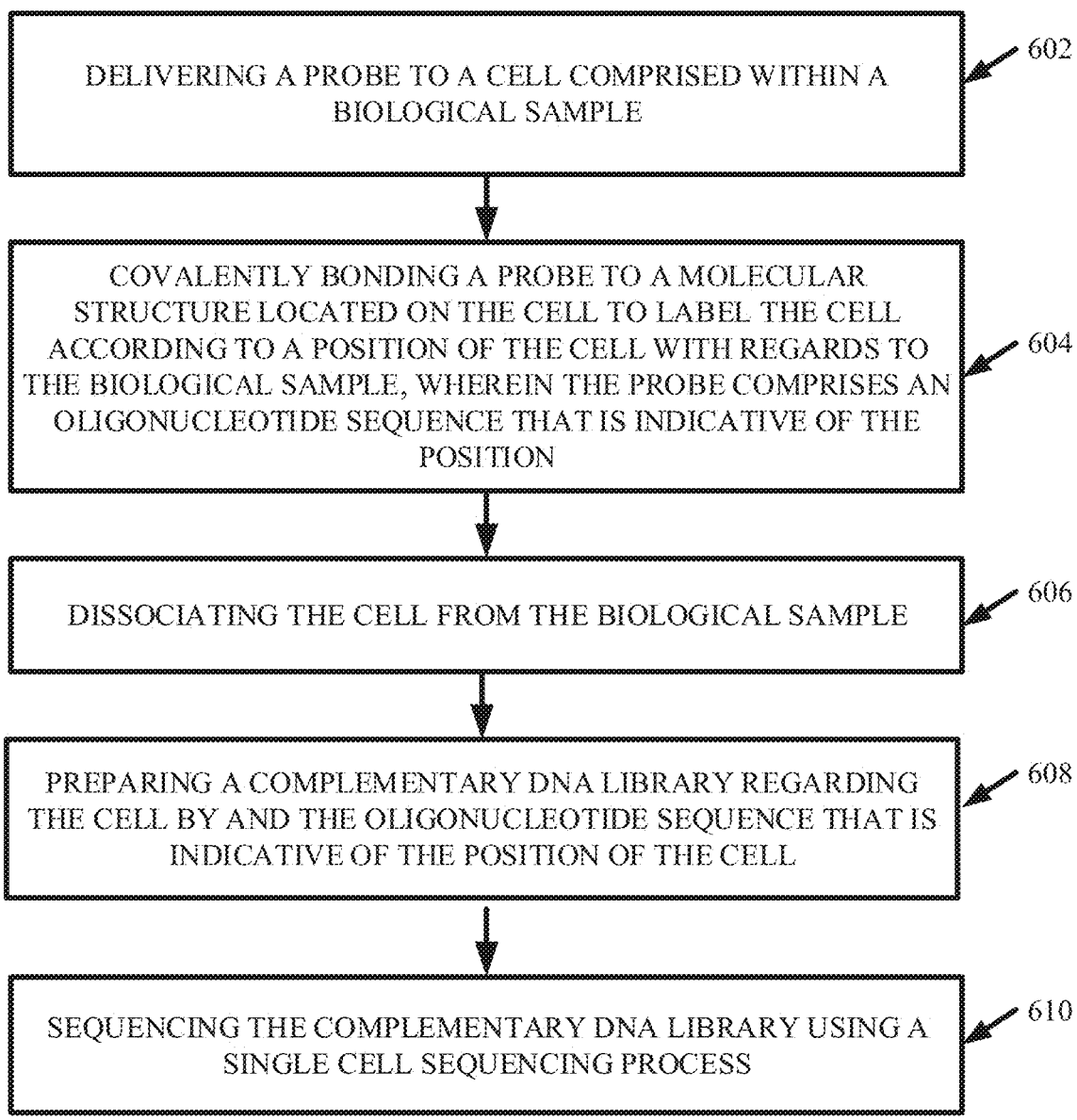
FIG. 6 illustrates a flow diagram of an example, non-limiting method that can facilitate labeling one or more cells based on the cells' position within a biological sample in accordance with one or more embodiments described herein.

FIG. 6 illustrates a flow diagram of an example, non-limiting method 600 that can facilitate labeling one or more cells (e.g., adherent cells 302) with one or more molecular probes 104 that can encode position information describing the cell in accordance with one or more embodiments described herein. Repetitive description of like elements employed in other embodiments described herein is omitted for sake of brevity. For example, in one or more embodiments the method 600 can be performed in accordance with one or more features of the labeling process 100.

At 602, the method 600 can comprise delivering one or more probes (e.g., one or more molecular probes 104) to one or more cells (e.g., one or more adherent cells 302) comprised within a biological sample 102. For example, the delivering at 602 can be performed by one or more delivery devices 114 that can dispense liquid cargo (e.g., comprising the one or more probes). For instance, the one or more delivery devices 114 can be microfluidic probes (e.g., as shown in FIG. 1). In various embodiments, the one or more probes (e.g., one or more molecular probes 104) can be delivered to various regions 202 of the biological sample 102.

At 604, the method 600 can comprise covalently bonding the one or more probes (e.g., one or more molecular probes 104) to one or more molecular structures (e.g., surface structures 418) located on the cell (e.g., one or more adherent cells 302) to label the cell according to a position of the cell with regards to the biological sample 102. The one or more probes (e.g., one or more molecular probes 104) can comprise an oligonucleotide sequence that can be indicative of the position of the cell (e.g., a position-specific oligonucleotide sequence, as described herein). For example, the covalent bonding at 604 can be performed in accordance with the illustration and/or description regarding FIG. 3 provided herein. For instance, wherein the one or more probes are delivered to multiple regions 202 during the delivery at 602, the composition of the oligonucleotide sequence (e.g., the position-specific oligonucleotide sequence) can be dependent on the region 202 in which the probe is delivered.

In various embodiments, the one or more probes can further comprise one or more of the following additional features: a functional group that can have a chemical affinity for the molecular structure, a polymerase chain reaction handle that can enable a polymerase chain reaction amplification, and/or a bonding oligonucleotide sequence that can be a complement to another oligonucleotide sequence of a distinctly coded microparticle (e.g., a complement to a capturing oligonucleotide sequence of a RNA capturing microparticle). The additional features can facilitate compatibility between the probe and one or more cDNA preparation methods using MMLV RT technology.

At 606, the method 600 can comprise dissociating one or more cells from the biological sample 102. For example, the cell can be dissociated into a single cell suspension. Despite being removed from its initial location within the biological sample 102, the dissociated cell can retain position information regarding the cell's initial location due to the position-specific oligonucleotide sequence of the one or more probes (e.g., molecular probes 104) covalently bonded to the cell.

At 608, the method 600 can comprise preparing a cDNA library regarding the cell and the oligonucleotide sequence that can be indicative of the position of the cell (e.g., to the position-specific oligonucleotide sequence of the molecular probe 104). For example, a MMLV RT technology can integrate the encoded position information defined by the position-specific oligonucleotide sequence to a RNA capturing microparticle (e.g., to the first oligonucleotide primer 404 of a bi-functionalized RNA capturing microparticle 402). Additionally, preparing the cDNA library at 608 can comprise applying the MMLV RT technology to one or more endogenous RNA sequences 403 also captured by the RNA capturing microparticle. For example, the MMLV RT technology can integrate the transcriptomic information of the endogenous RNA sequences 403 to the RNA capturing microparticle (e.g., to the second oligonucleotide primer 406 of a bi-functionalized RNA capturing microparticle 402).

At 610, the method 600 can comprise sequencing the cDNA library using one or more single cell sequencing processes. The single cell sequencing can comprise sequencing position information and a transcriptome for the one or more cells from the biological sample 102. For example, wherein one or more RNA capturing microparticles are used to prepare the cDNA library at 608, the sequencing at 610 can analyze the RNA capturing microparticles to record a transcriptome of the cell and an initial position of the cell within the biological sample 102. For instance, an integrated RNA capturing microparticle prepared at 608 can comprise various nucleotide sequences encoding: an identity of the subject cell by the cell barcode comprised within the second portion 410; an initial position of the cell within the biological sample 102 by an oligonucleotide sequence derived from the position-specific oligonucleotide sequence; and a transcriptome of the cell derived from the coding region 420 of one or more endogenous RNA sequences 403).

Figure 7:
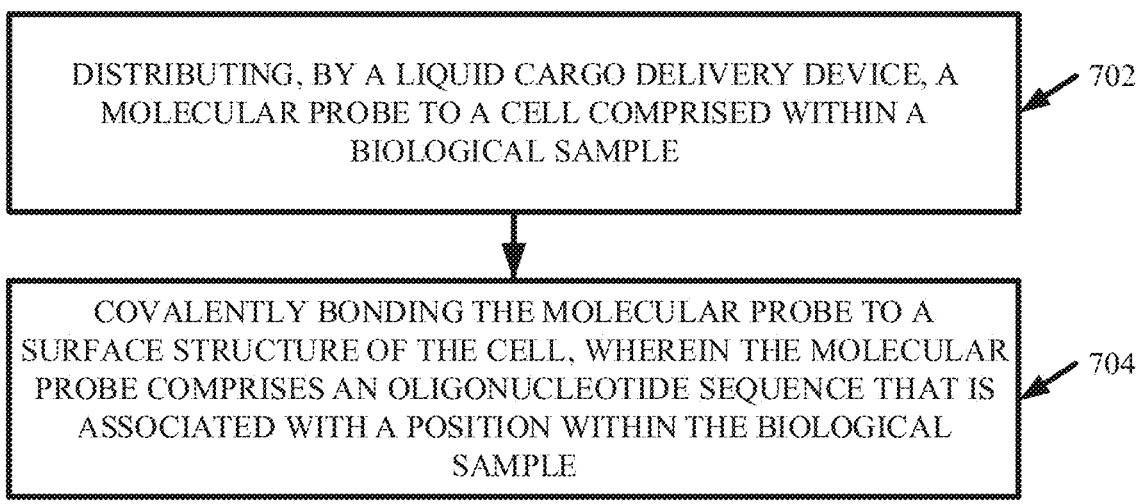
FIG. 7 illustrates a flow diagram of an example, non-limiting method that can facilitate labeling one or more cells based on the cells' position within a biological sample in accordance with one or more embodiments described herein.

FIG. 7 illustrates a flow diagram of an example, non-limiting method 700 that can facilitate labeling one or more cells (e.g., adherent cells 302) with one or more molecular probes 104 that can encode position information describing the cell in accordance with one or more embodiments described herein. Repetitive description of like elements employed in other embodiments described herein is omitted for sake of brevity. For example, in one or more embodiments the method 700 can be performed in accordance with one or more features of the labeling process 100.

At 702, the method 700 can comprise distributing, by one or more liquid cargo delivery devices (e.g., one or more delivery devices 114), one or more molecular probes 104 to one or more cells (e.g., one or more adherent cells 302) comprised within a biological sample 102. For instance, the one or more delivery devices 114 can be microfluidic probes (e.g., as shown in FIG. 1), wherein the one or more microfluidic probes can hydrodynamically localize as little as 100 picoliters of liquid cargo (e.g., comprising the one or more molecular probes 104) with micrometer precision. In various embodiments, the one or more probes (e.g., one or more molecular probes 104) can be delivered to various regions 202 of the biological sample 102.

At 704, the method 700 can comprise covalently bonding the one or more molecular probes 104 to one or more surface structures 418 of the one or more cells. The one or more surface structures 418 can be, for example, proteins or lipids located on a surface of the one or more cells. Also, the covalent bonding at 704 can be facilitated by ester coupling, thiol coupling, carboxylic acid coupling, hydrazine coupling, alkoxyamine coupling, and/or photoreactive crosslink coupling as described herein with regards to various embodiments. For example, the one or more molecular probes 104 can comprise one or more functional groups (e.g., amine reactive groups, thiol reactive groups, carboxylic acid reactive groups, aldehyde reactive groups, and/or photoreactive crosslinking groups) with a chemical affinity to the one or more surface structures 418.

Additionally, the one or more molecular probes 104 can comprise an oligonucleotide sequence that can be associated with a position within the biological sample 102 (e.g., a position-specific oligonucleotide sequence). For example, the biological sample 102 can be defined by a plurality of regions 202 (e.g., as shown in FIG. 2), wherein a respective oligonucleotide sequence can be associated with each region 202, thereby the oligonucleotide sequences can be position-specific. The position-specific oligonucleotide sequence associated with each region 202 can be different than the respective position-specific oligonucleotide sequences associated with the other regions 202. Molecular probes 104 distributed to a region 202 can comprise the position-specific oligonucleotide sequence associated with that region 202. Thus, cells located in a region 202 can be labeled with a position-specific oligonucleotide sequence associated with the given region 202 (e.g., via the covalent bonding at 704); thereby encoding position information of the cell onto the surface of the cell.

In various embodiments, the one or more probes can further comprise one or more of the following additional features: a polymerase chain reaction handle that can enable a polymerase chain reaction amplification, and/or a bonding oligonucleotide sequence that can be a complement to another oligonucleotide sequence of a distinctly coded microparticle (e.g., a complement to a capturing oligonucleotide sequence of a RNA capturing microparticle). The additional features can facilitate compatibility between the probe and one or more cDNA preparation methods using MMLV RT technology.

Figure 8:
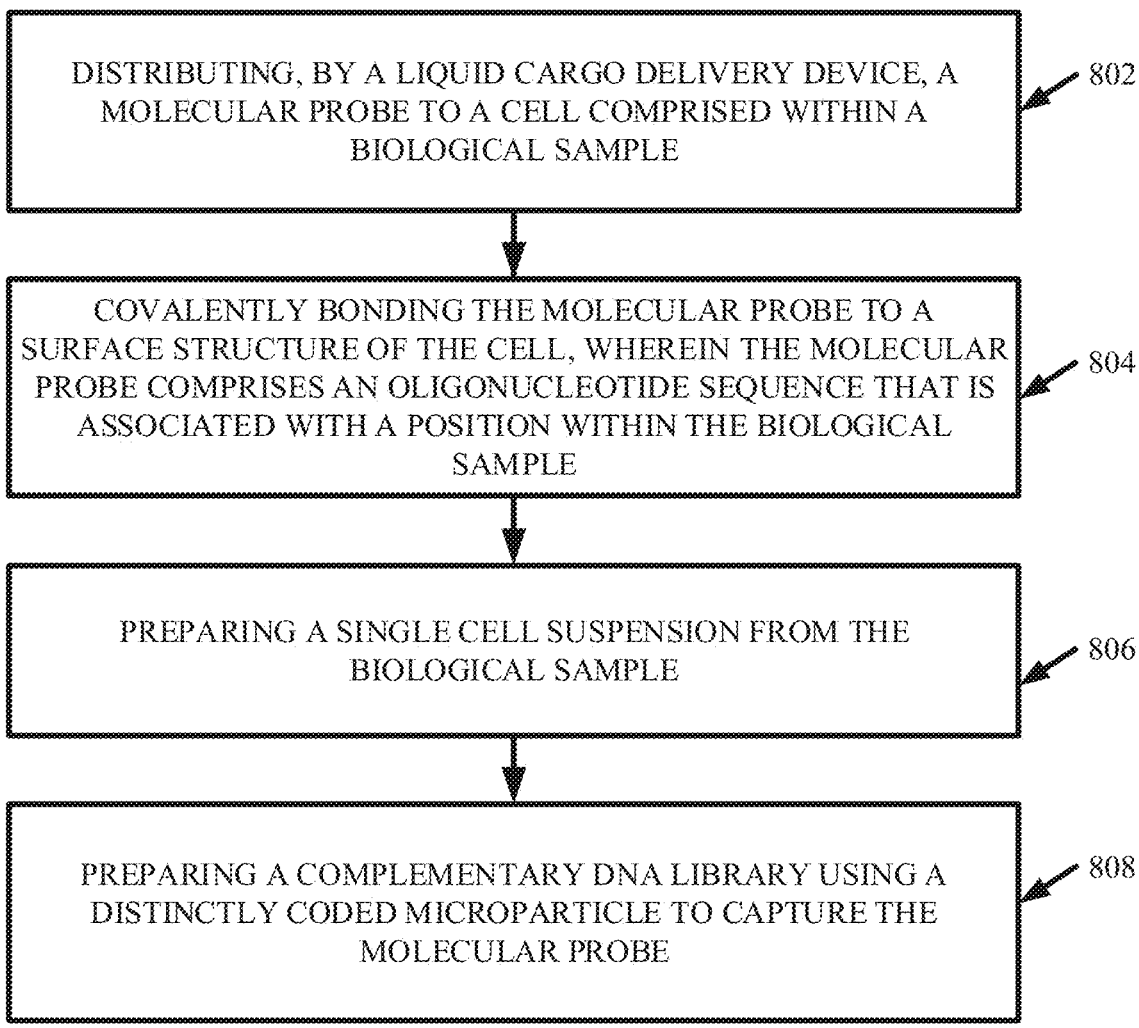
FIG. 8 illustrates a flow diagram of an example, non-limiting method that can facilitate labeling one or more cells based on the cells' position within a biological sample in accordance with one or more embodiments described herein.

FIG. 8 illustrates a flow diagram of an example, non-limiting method 800 that can facilitate labeling one or more cells (e.g., adherent cells 302) with one or more molecular probes 104 that can encode position information describing the cell in accordance with one or more embodiments described herein. Repetitive description of like elements employed in other embodiments described herein is omitted for sake of brevity. For example, in one or more embodiments the method 800 can be performed in accordance with one or more features of the labeling process 100.

At 802, the method 800 can comprise distributing, by one or more liquid cargo delivery devices (e.g., one or more delivery devices 114), one or more molecular probes 104 to one or more cells (e.g., one or more adherent cells 302) comprised within a biological sample 102. For instance, the one or more delivery devices 114 can be microfluidic probes (e.g., as shown in FIG. 1), wherein the one or more microfluidic probes can hydrodynamically localize as little as 100 picoliters of liquid cargo (e.g., comprising the one or more molecular probes 104) with micrometer precision. In various embodiments, the one or more probes (e.g., one or more molecular probes 104) can be delivered to various regions 202 of the biological sample 102.

At 804, the method 800 can comprise covalently bonding the one or more molecular probes 104 to one or more surface structures 418 of the one or more cells. The one or more surface structures 418 can be, for example, proteins or lipids located on a surface of the one or more cells. Also, the covalent bonding at 804 can be facilitated by ester coupling, thiol coupling, carboxylic acid coupling, hydrazine coupling, alkoxyamine coupling, and/or photoreactive crosslink coupling as described herein with regards to various embodiments. For example, the one or more molecular probes 104 can comprise one or more functional groups (e.g., amine reactive groups, thiol reactive groups, carboxylic acid reactive groups, aldehyde reactive groups, and/or photoreactive crosslinking groups) with a chemical affinity to the one or more surface structures 418.

Additionally, the one or more molecular probes 104 can comprise an oligonucleotide sequence that can be associated with a position within the biological sample 102 (e.g., a position-specific oligonucleotide sequence). For example, the biological sample 102 can be defined by a plurality of regions 202 (e.g., as shown in FIG. 2), wherein a respective oligonucleotide sequence can be associated with each region 202, thereby the oligonucleotide sequences can be position-specific. The position-specific oligonucleotide sequence associated with each region 202 can be different than the respective position-specific oligonucleotide sequences associated with the other regions 202. Molecular probes 104 distributed to a region 202 can comprise the position-specific oligonucleotide sequence associated with that region 202. Thus, cells located in a region 202 can be labeled with a position-specific oligonucleotide sequence associated with the given region 202 (e.g., via the covalent bonding at 804); thereby encoding position information of the cell onto the surface of the cell.

In various embodiments, the one or more probes can further comprise one or more of the following additional features: a polymerase chain reaction handle that can enable a polymerase chain reaction amplification, and/or a bonding oligonucleotide sequence that can be a complement to another oligonucleotide sequence of a distinctly coded microparticle (e.g., a complement to a capturing oligonucleotide sequence of a RNA capturing microparticle). The additional features can facilitate compatibility between the probe and one or more cDNA preparation methods using MMLV RT technology.

At 806, the method 800 can comprise preparing a single cell suspension from the biological sample 102. Despite being removed from an initial location within the biological sample 102, one or more cells dissociated from the biological sample 102 can retain position information regarding the cells' initial location due to the position-specific oligonucleotide sequence of the one or more molecular probes 104 covalently bonded to the cell at 804.

At 808, the method 800 can comprise preparing (e.g., by a MMLV RT technology) a cDNA library using a distinctly coded microparticle (e.g., a RNA capturing microparticle) to capture the molecular probe 104 bonded to the dissociated cell. For example, the preparing at 808 can comprise covalently bonding the molecular probe 104 to the distinctly coded microparticle (e.g., a RNA capturing microparticle). For instance, the bonding oligonucleotide sequence of the molecular probe 104 can complement a capturing oligonucleotide sequence of the distinctly coded microparticle (e.g., a RNA capturing microparticle), as described herein. Additionally, the preparing at 808 can comprise covalently bonding the distinctly coded microparticle (e.g., a RNA capturing microparticle) to an endogenous RNA sequence 403 of the dissociated cell. For instance, a tail portion 416 of the endogenous RNA sequence 403 can complement a capturing oligonucleotide sequence of the distinctly coded microparticle (e.g., a RNA capturing microparticle), as described herein. In one or more embodiments, the distinctly coded microparticle can be a bi-functionalized RNA capturing microparticle 402, which can capture both the molecular probe 104 and the endogenous RNA sequence 403 (e.g., as shown in FIG. 4). Furthermore, the method 800 can comprise performing one or more single cell sequencing techniques to analyze the distinctly coded microparticle and/or determine a combination of spatial and molecular measurements describing the one or more cells and the cells' initial position within the biological sample 102.

Figure 9:
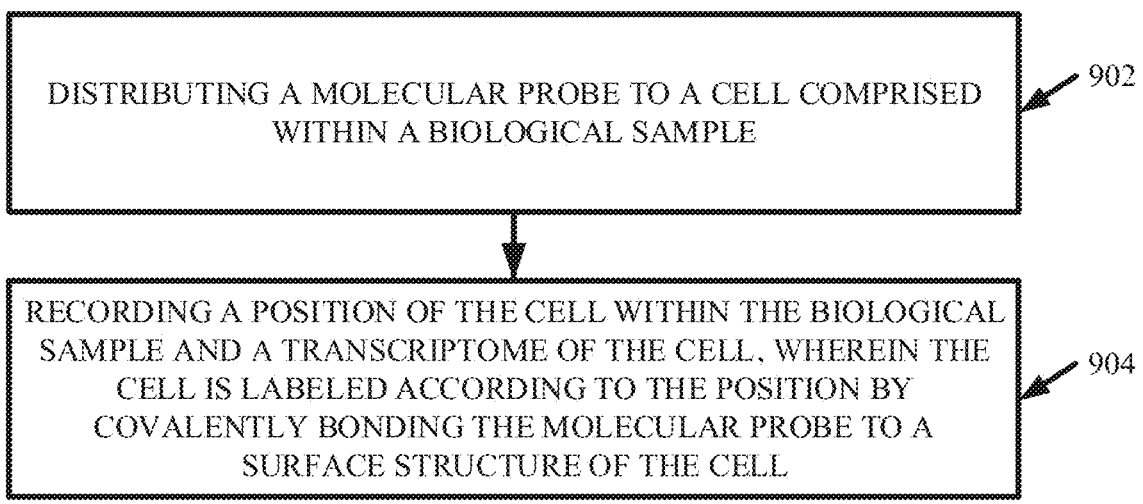
FIG. 9 illustrates a flow diagram of an example, non-limiting method that can facilitate recording a concomitant of positional and transcriptomic information regarding one or more cells within a biological sample in accordance with one or more embodiments described herein.

FIG. 9 illustrates a flow diagram of an example, non-limiting method 900 that can facilitate labeling one or more cells (e.g., adherent cells 302) with one or more molecular probes 104 that can encode position information describing the cell in accordance with one or more embodiments described herein. Repetitive description of like elements employed in other embodiments described herein is omitted for sake of brevity. For example, in one or more embodiments the method 900 can be performed in accordance with one or more features of the labeling process 100.

At 902, the method 900 can comprise distributing one or more molecular probes 104 to one or more cells (e.g., one or more adherent cell 302) comprised within a biological sample 102. For example, the delivering at 902 can be performed by one or more delivery devices 114 that can dispense liquid cargo (e.g., comprising the one or more probes). For instance, the one or more delivery devices 114 can be microfluidic probes (e.g., as shown in FIG. 1). In various embodiments, the one or more molecular probes 104 can be delivered to various regions 202 of the biological sample 102, wherein the composition of the molecular probes 104 can be dependent on the region 202 in which a subject molecular probe 104 is distributed.

At 904, the method 900 can comprise recording a position of one or more individual cells within the biological sample 102 and a transcriptome of the individual cells, wherein the one or more cells can be labeled according to the position by covalently bonding the one or more molecular probes 104 to one or more surface structures 418 of the individual cell. For example, the one or more cells can be labeled in accordance with one or more embodiments of the labeling process 100 described herein. To facilitate the recording at 904, the one or more cells, once labeled by the one or more molecular probes 104, can be disassociated from the biological sample 102. For instance, the labeled cell can be dissociated to form a single cell suspension.

Further, the recording at 904 can be facilitated by preparing a functionalized distinctly coded microparticle (e.g., a RNA capturing microparticle) using one or more MMLV RT technologies. For example, the distinctly coded microparticle (e.g., a RNA capturing microparticle, such as bi-functionalized RNA capturing microparticle 402) can capture (e.g., covalently bond to) both the molecular probe 104 and an endogenous RNA sequence 403 of the cell. Subsequently, the MMLV RT technology can functionalize the distinctly coded microparticle by integrating, into one or more oligonucleotide sequence primers of the distinctly coded microparticle: a complementary position-specific oligonucleotide sequence derived from a position-specific oligonucleotide sequence of the molecular probe 104; and a cDNA sequence derived from a coding region 420 of the endogenous RNA sequence 403. One or more single cell sequencing techniques (e.g., drop-seq and/or seq-well) can be utilized to analyze the functionalized distinctly coded microparticle and sort the encoded transcriptomic information and position information in silico.

Figure 10:
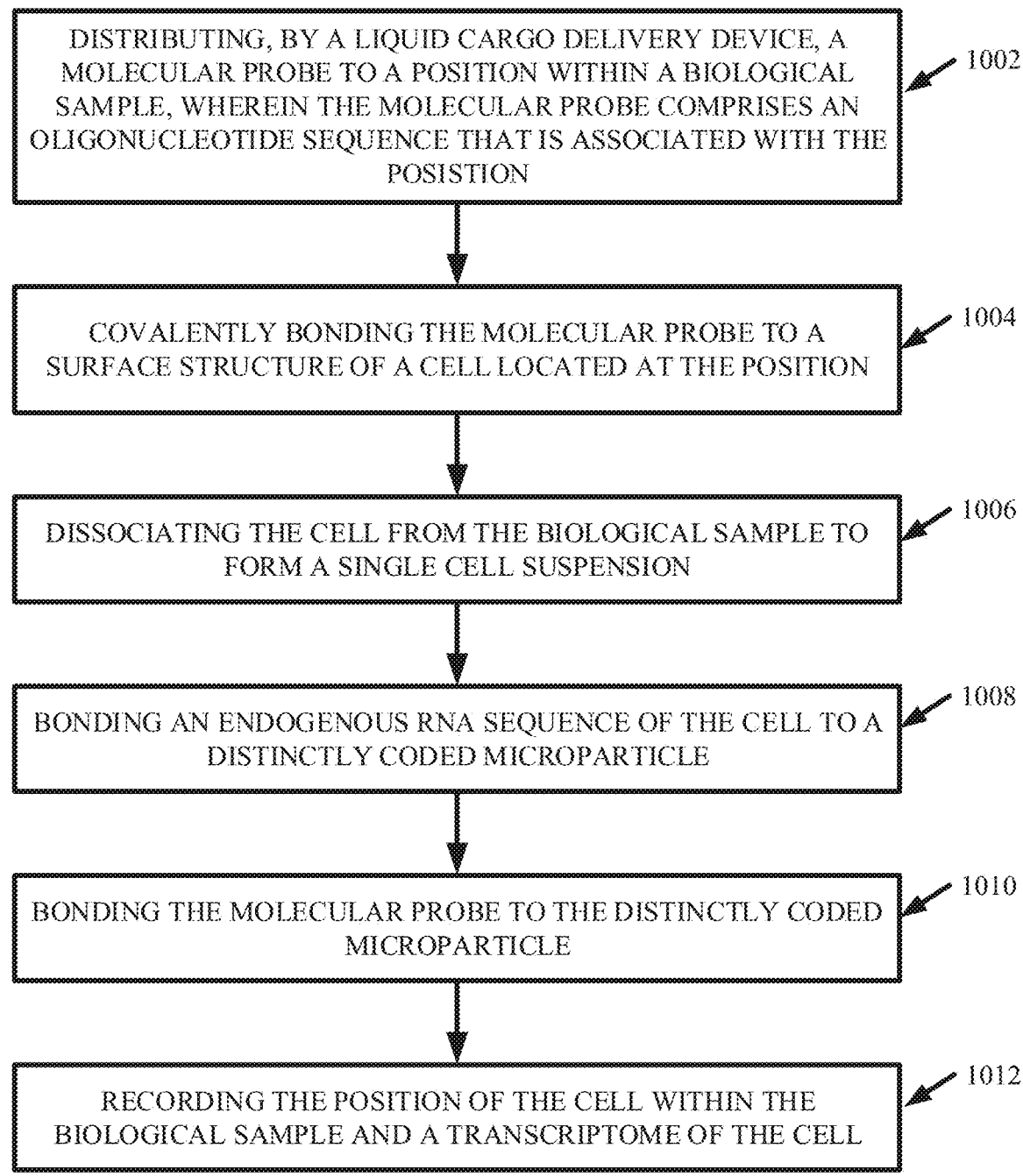
FIG. 10 illustrates a flow diagram of an example, non-limiting method that can facilitate recording a concomitant of positional and transcriptomic information regarding one or more cells within a biological sample in accordance with one or more embodiments described herein.

FIG. 10 illustrates a flow diagram of an example, non-limiting method 1000 that can facilitate labeling one or more cells (e.g., adherent cells 302) with one or more molecular probes 104 that can encode position information describing the cell in accordance with one or more embodiments described herein. Repetitive description of like elements employed in other embodiments described herein is omitted for sake of brevity. For example, in one or more embodiments the method 1000 can be performed in accordance with one or more features of the labeling process 100.

At 1002, the method 1000 can comprise distributing, by a liquid cargo delivery device, one or more molecular probes 104 to a position within a biological sample 102, wherein the one or more molecular probes 104 can comprise an oligonucleotide sequence associated with the position. For example, the biological sample 102 can be defined by a plurality of regions 202 (e.g., as shown in FIG. 2), wherein the oligonucleotide sequence can be associated with a region 202, from the plurality of regions 202, that comprises the position within the biological sample 102; thereby the oligonucleotide sequences can be position-specific.

At 1004, the method 1000 can comprise covalently bonding the one or more molecular probes 104 to one or more surface structures 418 of one or more cells located at the position. The one or more surface structures 418 can be, for example, proteins or lipids located on a surface of the one or more cells. Also, the covalent bonding at 1004 can be facilitated by ester coupling, thiol coupling, carboxylic acid coupling, hydrazine coupling, alkoxyamine coupling, and/or photoreactive crosslink coupling as described herein with regards to various embodiments. For example, the one or more molecular probes 104 can comprise one or more functional groups (e.g., amine reactive groups, thiol reactive groups, carboxylic acid reactive groups, aldehyde reactive groups, and/or photoreactive crosslinking groups) with a chemical affinity to the one or more surface structures 418.

At 1006, the method 1000 can comprise dissociating the cell from the biological sample 102 to form a single cell suspension. At 1006, the dissociated cell can retain position information regarding the cell's initial location, despite being removed from the initial location, at least due to the position-specific oligonucleotide sequence of the one or more molecular probes 104 covalently bonded to the cell at 1004.

At 1008, the method 1000 can comprise bonding an endogenous RNA sequence 403 of the cell to a distinctly coded microparticle (e.g., a RNA capturing microparticle, such as the bi-functionalized RNA capturing microparticle 402). For instance, a tail portion 416 of the endogenous RNA sequence 403 can complement a capturing oligonucleotide sequence of the distinctly coded microparticle (e.g., a RNA capturing microparticle), as described herein.

At 1010, the method 1000 can comprise bonding the one or more molecular probes 104 to the distinctly coded microparticle (e.g., a RNA capturing microparticle, such as the bi-functionalized RNA capturing microparticle 402). For instance, a bonding oligonucleotide sequence (e.g., comprised within the fourth section 112) of the molecular probe 104 can complement a capturing oligonucleotide sequence of the distinctly coded microparticle (e.g., a RNA capturing microparticle), as described herein.

At 1012, the method 1000 can comprise recording the position of the cell within the biological sample 102 and a transcriptome of the cell. For example, the recording at 1012 can be facilitated by functionalizing the distinctly coded microparticle using one or more MMLV RT technologies. For instance, the MMLV RT technology can functionalize the distinctly coded microparticle by integrating, into one or more oligonucleotide sequence primers of the distinctly coded microparticle: a complementary position-specific oligonucleotide sequence derived from a position-specific oligonucleotide sequence of the molecular probe 104; and a cDNA sequence derived from a coding region 420 of the endogenous RNA sequence 403. One or more single cell sequencing techniques (e.g., drop-seq and/or seq-well) can be utilized to analyze the functionalized distinctly coded microparticle and/or sort the encoded transcriptomic information and/or position information in silico.

In one or more embodiments, the one or more single cell sequencing techniques described herein can utilize one or more computer executable programs (e.g., performed by a system operably coupled to a processor) to read the position information encoded by the one or more molecular probes 104 and assign the transcriptomic information of a cell to the position in the biological sample 102 associated with the position information. For example, each respective region 202 of the biological sample 102 can be assigned transcriptomic information from the cells comprised within the given region 202. For instance, one or more single cell sequencing program can collect the transcriptomic information (e.g., derived from one or more endogenous RNA sequences captured by a RNA capturing molecule) and position information (e.g., derived from one or more molecular probes 104 captured by the RNA capturing molecule) of a cell (e.g., using one or more MMLV RT technologies in conjunction with one or more RNA capturing molecules) and assign the transcriptomic information to a region 202 of the biological sample 102 based on the position information. Further, the one or more single cell sequencing programs can execute the described collection and/or analysis with regards to multiple cells to establish a biological profile characterizing the biological sample (e.g., at least partially and/or in totality). Thereby, the one or more single cell sequencing programs can correlate transcriptomic information of one or more cells to positions (e.g., regions 202) within a subject biological sample 102.

Figure 11:
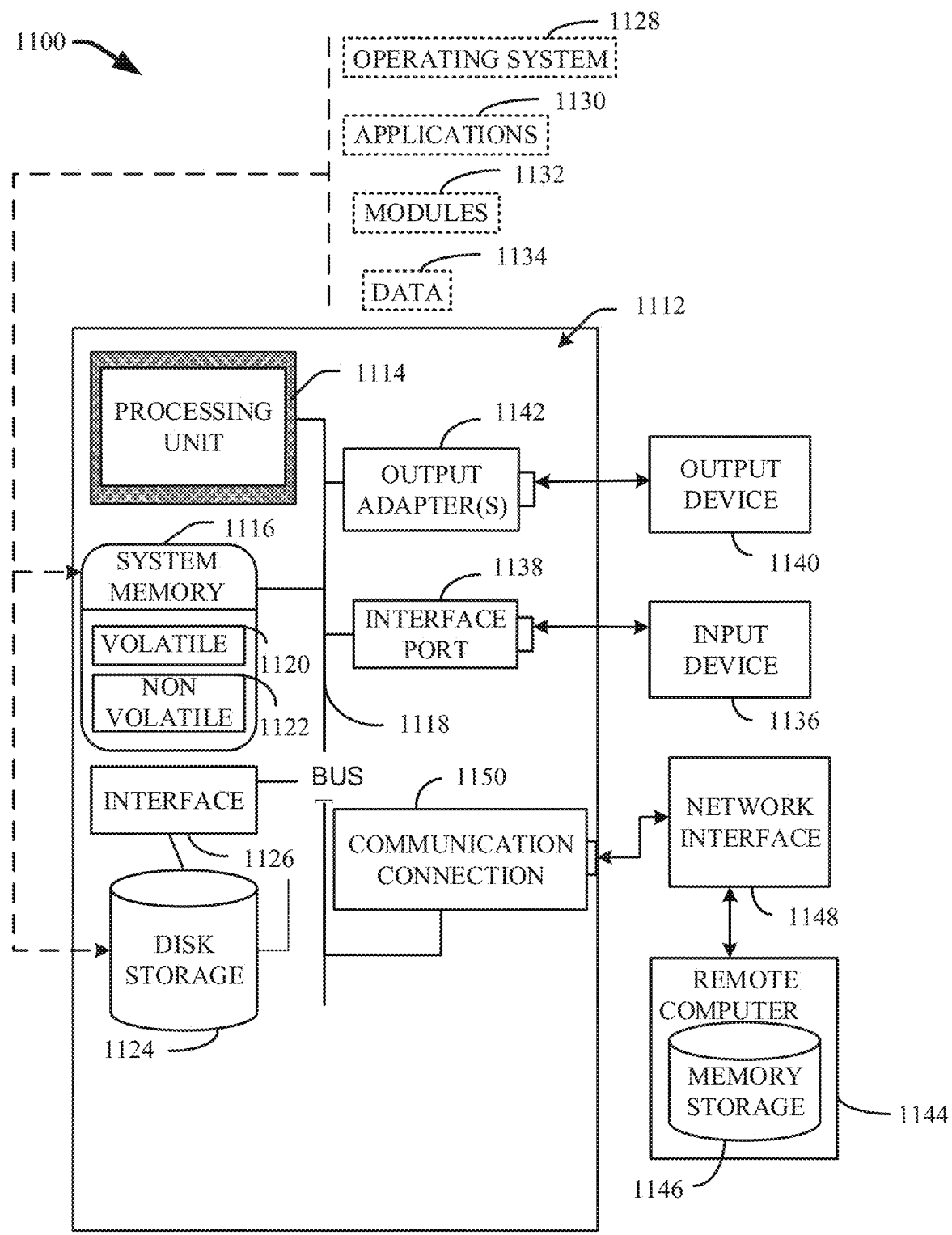
FIG. 11 illustrates a block diagram of an example, non-limiting operating environment in which one or more embodiments described herein can be facilitated

In order to provide a context for the various aspects of the disclosed subject matter, FIG. 11 as well as the following discussion are intended to provide a general description of a suitable environment in which the various aspects of the disclosed subject matter can be implemented. FIG. 11 illustrates a block diagram of an example, non-limiting operating environment in which the one or more single cell sequencing techniques (e.g., the one or more single cell sequencing programs) can be facilitated. Repetitive description of like elements employed in other embodiments described herein is omitted for sake of brevity. With reference to FIG. 11, a suitable operating environment 1100 for implementing various aspects of this disclosure, such as in silico analysis of transcriptomic information and/or position information made available by the various embodiments described herein, can executed and/or facilitated by a computer 1112. The computer 1112 can also include a processing unit 1114, a system memory 1116, and a system bus 1118. The system bus 1118 can operably couple system components including, but not limited to, the system memory 1116 to the processing unit 1114. The processing unit 1114 can be any of various available processors. Dual microprocessors and other multiprocessor architectures also can be employed as the processing unit 1114. The system bus 1118 can be any of several types of bus structures including the memory bus or memory controller, a peripheral bus or external bus, and/or a local bus using any variety of available bus architectures including, but not limited to, Industrial Standard Architecture (ISA), MicroChannel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1116 can also include volatile memory 1120 and nonvolatile memory 1122. The basic input/output system (BIOS), containing the basic routines to transfer information between elements within the computer 1112, such as during start-up, can be stored in nonvolatile memory 1122. By way of illustration, and not limitation, nonvolatile memory 1122 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1120 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1112 can also include removable/non-removable, volatile/non-volatile computer storage media. FIG. 11 illustrates, for example, a disk storage 1124. Disk storage 1124 can also include, but is not limited to, devices like a magnetic disk drive, floppy disk drive, tape drive, Jaz drive, Zip drive, LS-100 drive, flash memory card, or memory stick. The disk storage 1124 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1124 to the system bus 1118, a removable or non-removable interface can be used, such as interface 1126. FIG. 11 also depicts software that can act as an intermediary between users and the basic computer resources described in the suitable operating environment 1100. Such software can also include, for example, an operating system 1128. Operating system 1128, which can be stored on disk storage 1124, acts to control and allocate resources of the computer 1112. System applications 1130 can take advantage of the management of resources by operating system 1128 through program modules 1132 and program data 1134, e.g., stored either in system memory 1116 or on disk storage 1124. It is to be appreciated that this disclosure can be implemented with various operating systems or combinations of operating systems. A user enters commands or information into the computer 1112 through one or more input devices 1136. Input devices 1136 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1114 through the system bus 1118 via one or more interface ports 1138. The one or more Interface ports 1138 can include, for example, a serial port, a parallel port, a game port, and a universal serial bus (USB). One or more output devices 1140 can use some of the same type of ports as input device 1136. Thus, for example, a USB port can be used to provide input to computer 1112, and to output information from computer 1112 to an output device 1140. Output adapter 1142 can be provided to illustrate that there are some output devices 1140 like monitors, speakers, and printers, among other output devices 1140, which require special adapters. The output adapters 1142 can include, by way of illustration and not limitation, video and sound cards that provide a means of connection between the output device 1140 and the system bus 1118. It should be noted that other devices and/or systems of devices provide both input and output capabilities such as one or more remote computers 1144.

Computer 1112 can operate in a networked environment using logical connections to one or more remote computers, such as remote computer 1144. The remote computer 1144 can be a computer, a server, a router, a network PC, a workstation, a microprocessor based appliance, a peer device or other common network node and the like, and typically can also include many or all of the elements described relative to computer 1112. For purposes of brevity, only a memory storage device 1146 is illustrated with remote computer 1144. Remote computer 1144 can be logically connected to computer 1112 through a network interface 1148 and then physically connected via communication connection 1150. Further, operation can be distributed across multiple (local and remote) systems. Network interface 1148 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1150 refers to the hardware/software employed to connect the network interface 1148 to the system bus 1118. While communication connection 1150 is shown for illustrative clarity inside computer 1112, it can also be external to computer 1112. The hardware/software for connection to the network interface 1148 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A method, comprising:
   selectively delivering a probe to an adherent cell comprised within a biological sample at a regional position of the adherent cell within the biological sample; and
   covalently bonding the probe to a molecular structure located on the adherent cell to label the adherent cell according to the regional position, wherein the probe comprises an oligonucleotide sequence that is associated with the regional position within the biological sample.

2. The method of claim 1, wherein the probe further comprises:
a functional group that has a chemical affinity for the molecular structure;
a polymerase chain reaction handle that enables a polymerase chain reaction amplification; and
a bonding oligonucleotide sequence that complements another oligonucleotide sequence of a distinctly coded microparticle.

3. The method of claim 2, wherein the functional group is a compound selected from a group consisting of an amine reactive compound, a thiol reactive compound, carboxylic acid reactive compounds, aldehyde reactive compounds, and a photoreactive crosslinking compound, and wherein the molecular structure is a protein.

4. The method of claim 1, further comprising:
covalently bonding a second probe to a second molecular structure located on a second adherent cell to label the second adherent cell according to a second regional position within the biological sample, wherein the second adherent cell is comprised within the biological sample, and wherein the second probe comprises a second oligonucleotide sequence that is associated with the second regional position.

5. The method of claim 1, wherein the selectively delivering the probe is performed using a microfluidic probe.

6. The method of claim 1, further comprising:
dissociating the adherent cell from the biological sample subsequent to the covalent bonding;
preparing a complementary deoxyribonucleic acid library regarding the adherent cell and the oligonucleotide sequence that is associated with the regional position; and
sequencing the complementary deoxyribonucleic acid library using a single cell sequencing process.

7. The method of claim 6, wherein the preparing comprises applying a Moloney murine leukemia virus transcriptase technology to the oligonucleotide sequence that is associated with the regional position.

8. A method, comprising:
distributing, by a liquid cargo delivery device, a molecular probe to an adherent cell comprised within a biological sample at a regional position of the adherent cell within the biological sample; and
covalently bonding the molecular probe to a surface structure of the adherent cell, wherein the molecular probe comprises an oligonucleotide sequence that is associated with the regional position within the biological sample.

9. The method of claim 8, wherein the molecular probe further comprises:
a functional group that chemically reacts with the surface structure of the adherent cell;
a polymerase chain reaction handle that enables a polymerase chain reaction amplification; and
a bonding oligonucleotide sequence that complements another oligonucleotide sequence of a distinctly coded microparticle.

10. The method of claim 9, wherein the functional group is a compound selected from a group consisting of an amine reactive compound, a thiol reactive compound, carboxylic acid reactive compounds, aldehyde reactive compounds, and a photoreactive crosslinking compound.

11. The method of claim 10, wherein the liquid cargo delivery device is a microfluidic probe, and wherein the surface structure is a protein.

12. The method of claim 11, further comprising:
preparing a single cell suspension from the biological sample; and
preparing a complementary deoxyribonucleic acid library using the distinctly coded microparticle to capture the molecular probe.

13. The method of claim 12, wherein the preparing the complementary deoxyribonucleic acid library comprises:
covalently bonding the molecular probe to the distinctly coded microparticle; and
covalently bonding the distinctly coded microparticle to an endogenous ribonucleic acid sequence of the single cell suspension.

14. A method, comprising:
selectively delivering a molecular probe to an adherent cell comprised within a biological sample at a regional position of the adherent cell within the biological sample; and
recording the regional position of the adherent cell within the biological sample and a transcriptome of the adherent cell, wherein the adherent cell is labeled according to the regional position by covalently bonding the molecular probe to a surface structure of the adherent cell, wherein the molecular probe comprises an oligonucleotide sequence that is associated with the regional position within the biological sample.

15. The method of claim 14, further comprising:
dissociating the adherent cell from the biological sample to form a single cell suspension;
bonding an endogenous ribonucleic acid sequence of the single cell suspension to a distinctly coded microparticle; and
bonding the molecular probe to the distinctly coded microparticle.

16. The method of claim 15, further comprising:
collecting, by a system operably coupled to a processor, the transcriptome via the endogenous ribonucleic acid sequence; and
assigning, by the system, the transcriptome to the position of the cell within the biological sample based on the molecular probe bonded to the distinctly coded microparticle with the endogenous ribonucleic acid sequence.

17. The method of claim 16, wherein the molecular probe further comprises:
a functional group that chemically reacts with the surface structure of the adherent cell;
a polymerase chain reaction handle that enables a polymerase chain reaction amplification; and
a bonding oligonucleotide sequence that complements another oligonucleotide sequence of the distinctly coded microparticle.

18. The method of claim 17, wherein the liquid cargo delivery device is a microfluidic probe, wherein the surface structure is a protein, and wherein the functional group is a compound selected from a group consisting of an amine reactive compound, a thiol reactive compound, carboxylic acid reactive compounds, aldehyde reactive compounds, and a photoreactive crosslinking compound.

* * * * *